United States Patent [19]

He

[11] Patent Number: 5,400,258
[45] Date of Patent: Mar. 21, 1995

[54] AUTOMATIC CROSS-DIRECTIONAL CONTROL ZONE ALIGNMENT FOR SHEETMAKING SYSTEMS

[75] Inventor: George X. He, Menlo Park, Calif.

[73] Assignee: Measurex Corporation, Cupertino, Calif.

[21] Appl. No.: 115,594

[22] Filed: Sep. 3, 1993

[51] Int. Cl.⁶ .................. G06F 15/46; G01L 5/04; D21F 11/00; G01N 21/84
[52] U.S. Cl. ..................... 364/471; 73/159; 162/198; 356/431; 356/429
[58] Field of Search ............... 364/468–473, 364/550–569; 73/159, 160, 789, 791; 250/557, 560, 571; 83/74, 365; 242/57.1; 162/263, 198; 156/64, 361, 495; 356/431, 429

[56] References Cited

U.S. PATENT DOCUMENTS

| | | | |
|---|---|---|---|
| Re. 32,967 | 6/1989 | St. John et al. | 242/57.1 |
| 4,586,372 | 5/1986 | Massen | 73/159 |
| 4,786,817 | 11/1988 | Boissevain et al. | 250/571 |
| 4,835,720 | 5/1989 | Ditto et al. | 364/561 |
| 4,903,528 | 2/1990 | Balakrishnan et al. | 73/159 |
| 4,921,574 | 5/1990 | Hu | 162/198 |
| 4,947,684 | 8/1990 | Balakrishnan | 73/159 |
| 4,947,686 | 8/1990 | Wendell et al. | 73/159 |
| 4,955,265 | 9/1990 | Nakasawa et al. | 83/74 |
| 4,965,736 | 10/1990 | Balakrishnan | 364/469 |
| 5,122,963 | 6/1992 | Chen | 364/471 |

Primary Examiner—Roy N. Envall, Jr.
Assistant Examiner—Jim Trammell
Attorney, Agent, or Firm—Burns, Doane, Swecker & Mathis

[57] ABSTRACT

A system for aligning control zones with measurement zones in a sheetmaking system having a plurality of actuators arranged in the cross-direction, comprising the steps of: a) bumping at least one of the actuators; b) measuring a profile of the sheet at a substantial distance from the bumped actuators; and c) determining a location of the effect of each of the bumped actuators on the sheet.

16 Claims, 4 Drawing Sheets

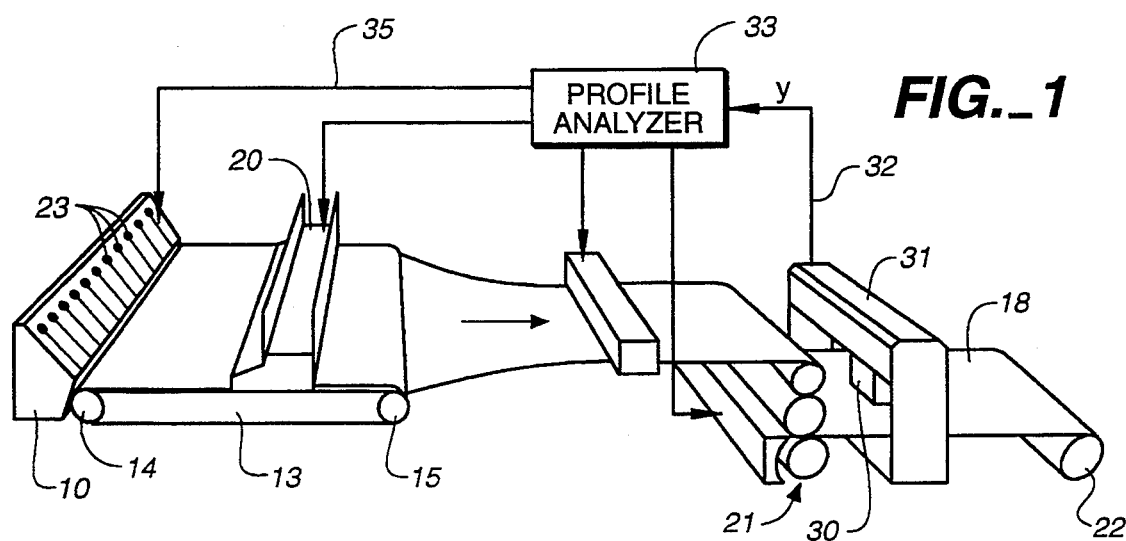
FIG._1
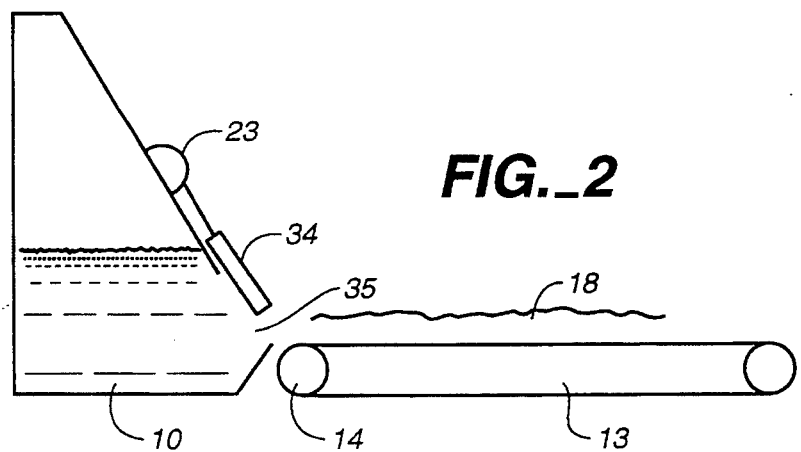
FIG._2
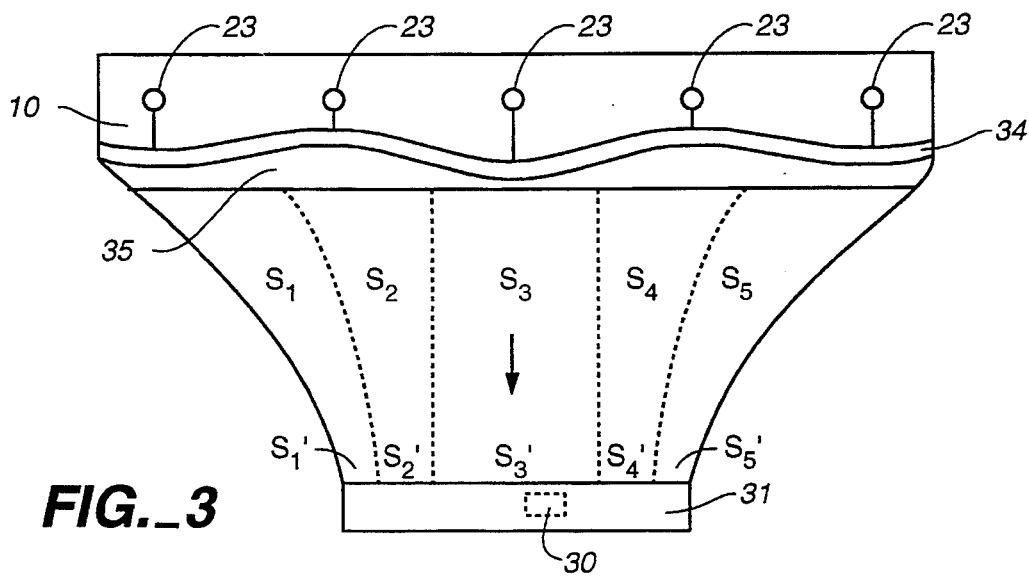
FIG._3

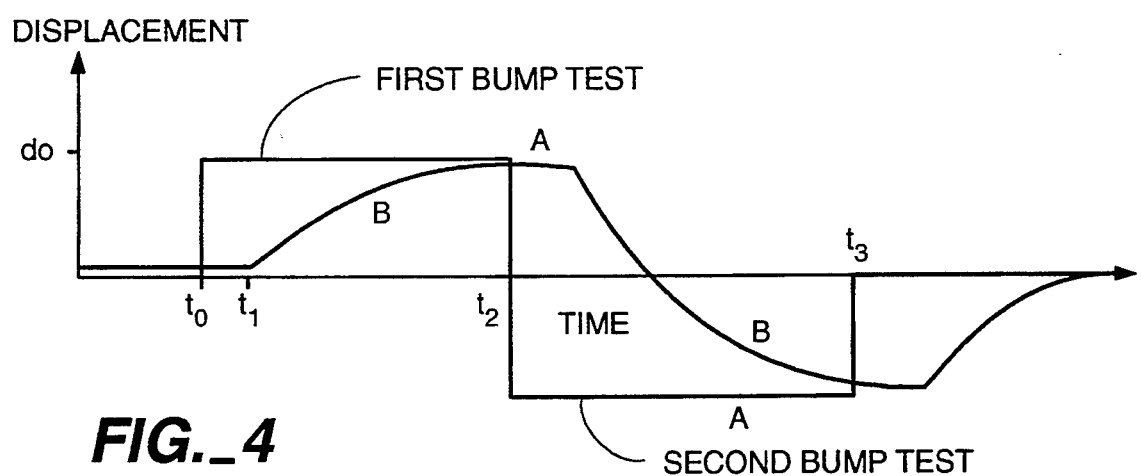
FIG._4
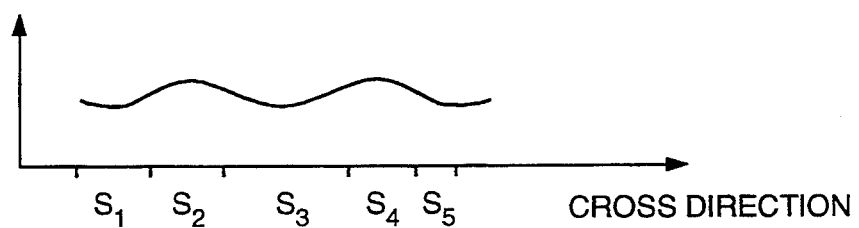
FIG._5
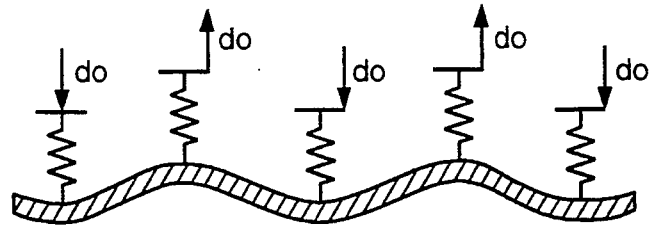
FIG._6
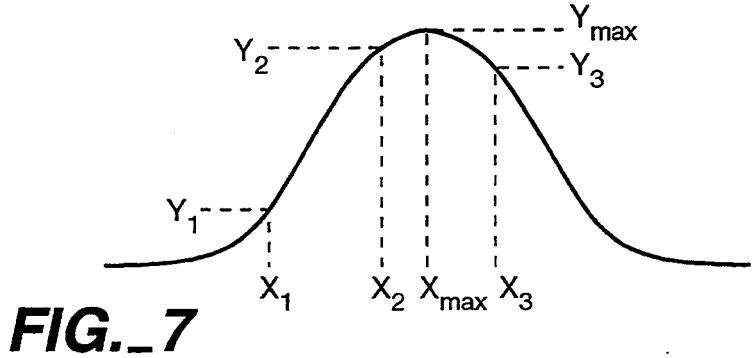
FIG._7

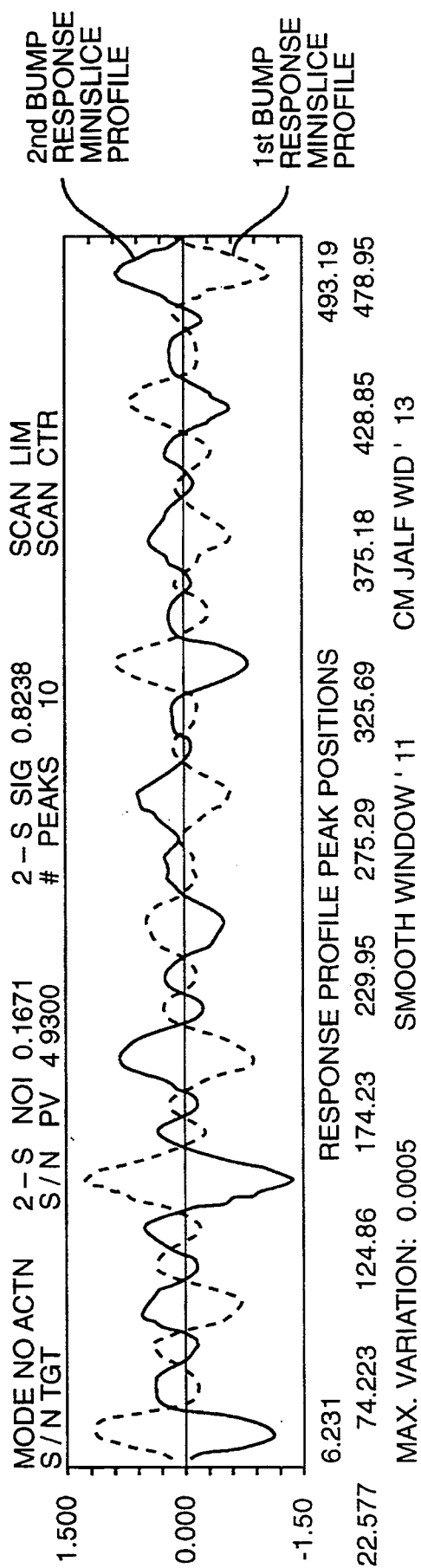
FIG._8A
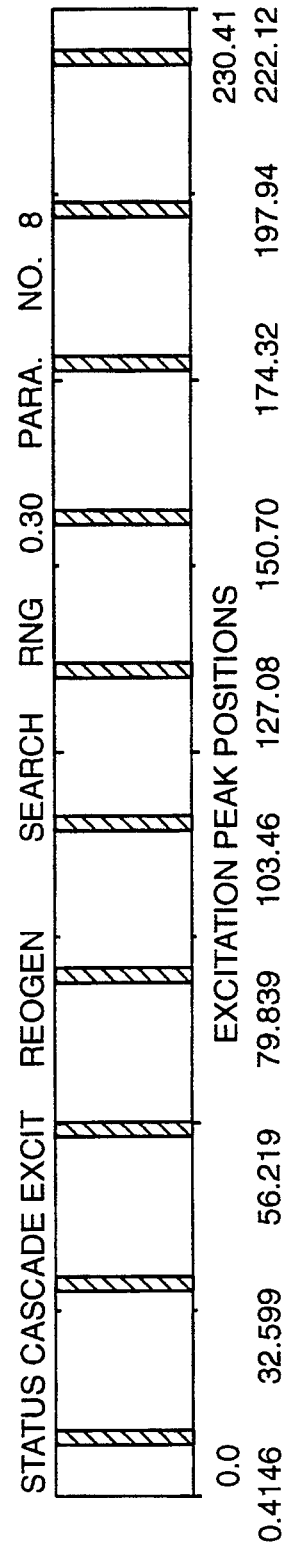
FIG._8B

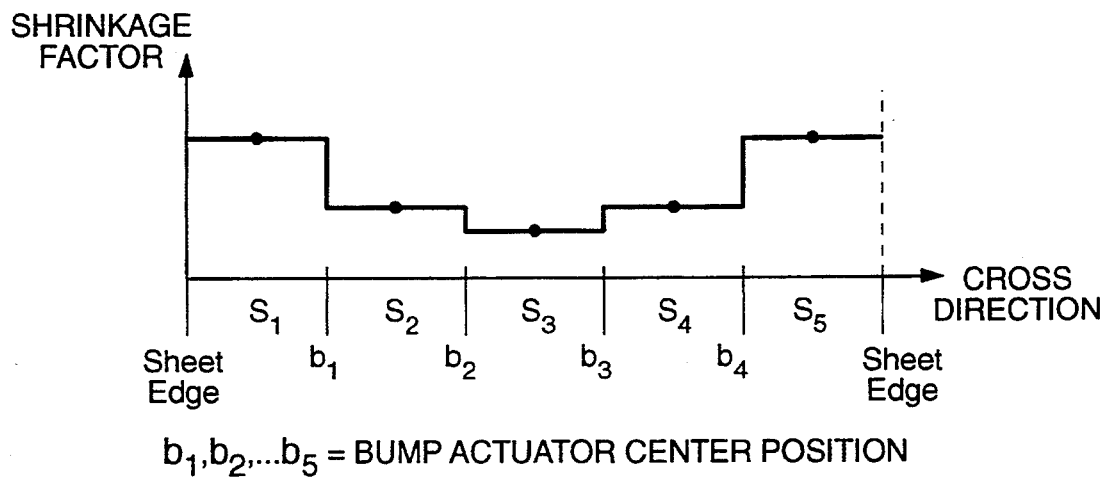
FIG._9A
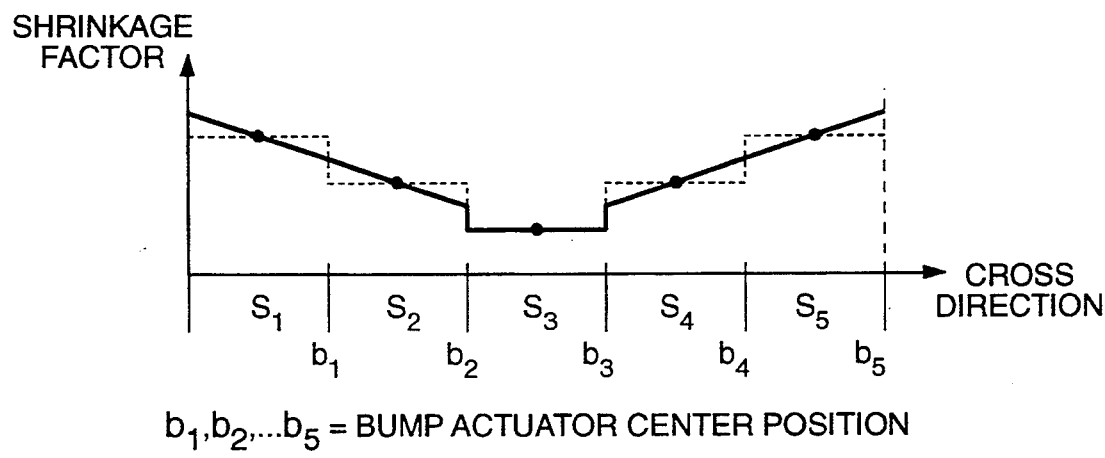
FIG._9B
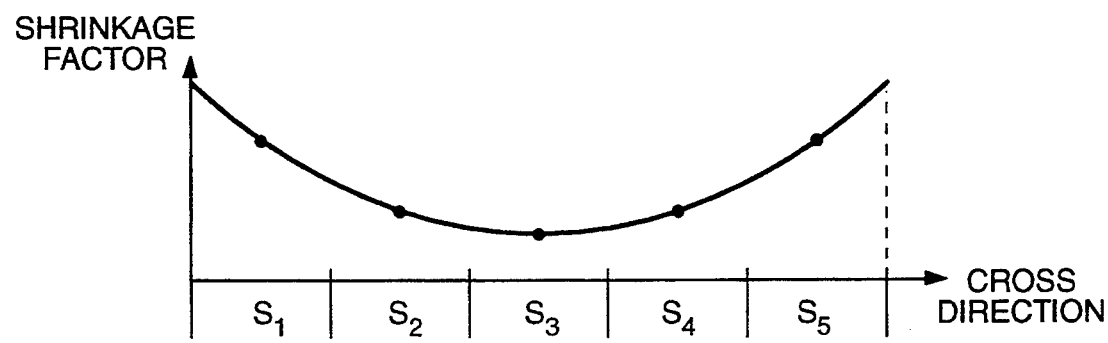
FIG._9C

AUTOMATIC CROSS-DIRECTIONAL CONTROL ZONE ALIGNMENT FOR SHEETMAKING SYSTEMS

BACKGROUND OF THE INVENTION

1. Field of the Invention

The present invention generally relates to a method and apparatus for aligning control zones in sheetmaking systems.

2. State of the Art

In modern automated paper making machines, continuous paper webs, sometimes measuring as much as four-hundred inches across, can be produced at rates of up to one-hundred feet per second. To control the quality of the paper manufactured at such rates and to reduce the quantity of finished product that must be rejected if there are upsets in the manufacturing process, properties of the paper web must be measured and adjusted while the machines are operating. That is, quality measurements and controls must be made on-line.

On-line measurements in sheetmaking manufacturing processes can be used for various purposes. For example, the on-line measurements can be employed as a basis for adjusting pulp feedstock composition, changing the quantity of steam or other heat applied to a paper web during production. The on-line measurements also can be employed as a basis for varying the nip pressure between calendaring rollers at the end of a papermaking process. In each of these examples, the on-line measurements are employed as a basis for operating control devices that affect sheet quality at various stages in a manufacturing process.

The control devices that are associated with modern papermaking machines include, for instance, feedboxes, steamboxes, and calendaring systems. Feedboxes operate to discharge the feedstock that forms the paper web. Steamboxes control the quantity of heat applied to the web. In a calendaring system, the calendaring rollers apply pressure at selected zones across the paper web.

On-line measurements in papermaking and other sheetmaking machines typically are categorized as either in the machine direction or in the cross direction. Machine-direction measurements reveal the sheet quality variation along the direction that a web travels during manufacture. Cross-directional measurements, on the other hand, reveal the variation across a web surface in a direction which is perpendicular to the machine direction.

Cross-directional measurements are typically made by scanning sensors that periodically move back and forth across the width of a travelling paper web. The sensors can be ones that measure sheet properties such as moisture content, caliper (i.e., thickness), and basis weight (i.e., mass per unit surface area). In the case of basis weight, travelling webs of sheet material are often measured by beta gauges that comprises a source of beta radiation (beta rays) and an ionization chamber. In operation, beta gauges are mounted on a sheetmaking machine in a position such that the beta rays are directed against one surface of a traveling web of sheet material while the ionization chamber is located for detecting the beta rays that have passed through the web from the source. The quantity of beta rays that are absorbed or transmitted over a given area of sheet material is a measure of the basis weight of the sheet material.

For conventional high-speed scanning sensors, a complete scan across a web typically requires between fifteen and thirty seconds. During a scan, measurements may be read from a sensor at intervals as frequent as fifty milliseconds. (Such intervals are referred to herein as minislice intervals.) A sequence of successive adjacent minislice measurements defines a measurement zone or slice.

In practice, control devices that are associated with sheet making machines normally include a series of actuator systems arranged in the cross direction. For example, in a typical feedbox, the control device is a flexible member or slice lip that extends laterally across a small gap at the bottom discharge port of the feedbox. The slice lip is movable for adjusting the area of the gap and, hence, for adjusting the rate at which feedstock is discharged from the feedbox. A typical slice lip is operated by a number of actuator systems, or cells, that operate to cause localized bending of the slice lip at spaced apart locations in the cross-direction. The localized bending of the slice lip member, in turn, determines the width of the feed gap at the various slices locations across the web.

It has been suggested that sheetmaking machines can be controlled by adjusting actuators using measurement signals provided by scanning sensors. In the case of cross direction control, for example, a commonly suggested control scheme is to measure values at selected cross direction locations on a sheet and then to compare those measured values to target or setpoint values. The difference for each pair of measured and setpoint values—the error—can be used for algorithmically generating appropriate outputs to cross direction control actuators to minimize the error. In such systems, a measurement zone is defined as the cross direction portion of sheet which is measured and used as feedback control for a cross direction actuator zone, and a control zone is defined as the portion of the sheet affected by a cross direction actuator zone.

In practice, it is difficult to control sheetmaking machines by adjusting actuators using measurement signals provided by scanning sensors. The difficulties particularly arise because the scanning sensors are separated from the control actuators by substantial distances in the machine direction. Because of such separations, it is difficult to determine which measurements zones are associated with which actuator zones. Such difficulties are referred to as alignment problems in the papermaking art. Alignment problems are exacerbated when, as is typical, there is uneven paper shrinkage of a paper web as it progresses through a papermaking process.

Another difficulty is that the effect of each actuator is not always limited within the corresponding control zone but spans over a few control zones. Knowing this effect is normally referred to an interzone coupling. The precise characteristics of the coupling effect and accomplishing algorithmic decoupling accordingly is almost as knowing crucial as the proper alignment.

One conventional method in papermaking for aligning actuator zones with measurement zones involves the use of dye tests. In a dye test, narrow streams of colored liquid are applied to feedstock as it flows beneath a slice lip. The dye streams initially form parallel lines that extend in the machine direction, but those lines may deviate from parallel if there is web shrinkage during the papermaking process. The dye marks passing through the measurement devices reveal the distribution of control zones and therefore specify the alignment of measurement zones.

Conventional dye tests, however, have numerous drawbacks. The most serious drawback is that the tests destroy finished product and, therefore, it is seldom feasible to perform dye tests at an intermediate point in a sheetmaking production run, even though sheetmaking processes are likely to drift out of control during such times. Further, because of the limited thickness and high absorption characteristics of tissue grades of paper, dye tests are typically limited to paper products that have relatively high weight grades.

SUMMARY OF THE PRESENT INVENTION

The present invention generally relates to systems for automatically and non-destructively mapping and aligning control zones and measurement zones in papermaking and other sheetmaking systems; that is, the present invention generally relates to systems for determining the correspondence between actuator zones and measurement zones, including interzone coupling, in papermaking and other sheetmaking systems. The present invention provides, for example, a system for mapping and aligning the slice lip actuator control zones with dry weight measurement zones in a papermaking machine. The alignment method can be employed before any process control is implemented, as well as, after the control system is up and running. The present invention can be employed in sheetmaking manufacturing operations such as those that produce paper, plastic film and sheet metal.

In one preferred embodiment, the present invention provides a method for aligning control zones with measurement zones in a sheetmaking system having a plurality of actuators arranged in the cross-direction, comprising the steps of: a) bumping at least two of the actuators; b) measuring a profile of the sheet by a scanner scanning the sheet at a substantial distance from the bumped actuators where the corresponding sheet properties are desired to be controlled; c) determining the alignment information including the location of the effect of each of the bumped actuators on the sheet-by pattern matching between the cross-direction actuator excitation profile and its response profile measured by the scanner scanning the sheet; d) providing the alignment information as a shrink factor array. The shrink factor array provides a set of coefficients for mapping, or transforming, measurement zones that are referenced to scanner frames to actuator zones referenced to profiling actuator devices; the method may include the further step of e) providing actuator effective gain and interzone coupling information using a filtered response profile array.

BRIEF DESCRIPTION OF THE DRAWINGS

The present invention can be further understood with reference to the following description in conjunction with the appended drawings, wherein like elements are provided with the same reference numerals. In the drawings:

FIG. 1 is a generally schematic view of a typical papermaking system;

FIG. 2 schematically shows a side view of a feedbox for use with the papermaking system of FIG. 1;

FIG. 3 schematically shows a top view of a portion of the papermaking process with a slice lip being illustrated with greatly exaggerated vertical displacements for exemplifying several displacements;

FIG. 4 is a graph which shows (A) the displacement of an actuator member from one operating point to another and (B) the corresponding sheet property response;

FIG. 5 is a graph of a cross-directional profile of measurements of a web of material produced by the system of FIG. 3;

FIG. 6 is a schematically depicts a slice lip member that has been deformed;

FIG. 7 second order polynomial for use in estimating a profile near a peak;

FIG. 8A shows examples of filtered responses of two bump tests;

FIG. 8B shows center positions of actuators that have been used for the two bump tests; and FIGS. 9A–9C illustrate several different techniques for assigning a shrinkage factor to control zones.

DESCRIPTION OF THE PREFERRED EMBODIMENTS

In FIG. 1, a machine for producing continuous web 18 of paper sheet material includes a feedbox 10, a steambox 20, a calendaring stack 21, and a take-up reel 22. In the feedbox 10, actuators are arranged to control the discharge of feedstock onto supporting web 13. The web 18 is trained to travel between rollers 14, 15 and to pass through a calendaring stack 21. The calendaring stack 21 includes actuators 24 that control the compressive pressure applied across the paper web. The finished sheet product is collected on a reel 22. In practice, the portion of the papermaking process near a feedbox is referred to as the wet end, while the portion of the process near a takeup reel is referred to as the dry end.

As further shown in the system in FIG. 1, a scanning sensor 30 is mounted on a frame 31 for periodically traversing the web while measuring its properties. It should be noted that the scanning sensor traverses the web in the cross direction. It also should be noted that the scanning sensor is located at the dry end of the process and, therefore, is at a substantial distance from the feedbox 10. In the embodiment shown in the drawings, the scanning sensor 30 is connected by line 32 to a profile analyzer 33 that processes the web measurements provided by the scanning sensor 30. In normal practice, the profile analyzer 33 provides output signals that are indicative of the magnitude of web properties—such as basis weight, caliper, or moisture content—at cross-directional measurement points. Also, as indicated in FIG. 1, the profile analyzer 33 can be connected for controlling actuators at one or more stages in the papermaking process. For instance, as indicated by line 35, signals from the profile analyzer can be provided for controlling the slice lip actuators 23.

As will now be described, the profile analyzer 33 includes a system for automatically aligning actuator influence intervals (zones) and measurement zones across the web 18. Ultimately, the system provides a shrink factor array that includes a set of coefficients for mapping, or transforming, measurement zones that are referenced to scanner frames to actuator zones referenced to profiling devices. Thus, for example, the sensor 30 can be operated for measuring the dry weight of a paper web and the sensor output signals can be manipulated by the profile analyzer for adjusting the slice lip actuators in a manner that controls the moisture content of the paper during production. In this example, then, the measurement zones would be correlated or aligned with individual ones of the slice lip actuators.

In accordance with the preceding example, FIGS. 2 and 3 depict a slice lip control system which is mounted on a feedbox 20 for controlling the extent to which a flexible slice lip member 34 extends across the discharge gap 35 at the base of the feedbox 10. In the embodiment shown in FIG. 3, the slice lip member 34 extends along the feedbox across the entire width of the web in the cross-direction. Also, in this embodiment, actuators 23 are arranged at spaced-apart locations along the length of the slice lip member 34 for causing local intervals of displacement (i.e., bending) of the slice lip member. It should be understood that the actuators 23 are independently operable. In practice, there are often more than fifty actuators arranged across the width of a sheet. The spacing between the actuators may or may not be uniform.

For present purposes, it may be understood that the spacing between the actuators 23 defines the control zones (or slices) across the web 18. The control zones across the web 18 are designated $S_1, S_2, \ldots S_5$ in FIG. 3. In that drawing, the dashed lines indicate boundaries between slices $S_1, S_2 \ldots S_5$ as the web travels in the direction of the arrow. The widths of the slices, with their mapping (shrinking) factors, specify the widths and position of the measurement zones to be mapped to the actuator zones.

In operation of a feed box such as the one depicted in FIGS. 2 and 3, the gap between the slice lip member 34 and the surface of the web 18, at any given control zone, is adjustable, by operating a selected one of the actuators 23. That is, an actuator can bend the slice lip member 34 toward or away from the web surface and such displacement, in turn, determines the effective area of the feedbox discharge gap 35. The area of the discharge gap 35 controls the flow rate of wet feedstock material which is fed onto supporting web 13. The feed flow rate ultimately affects the properties of the finished sheet material—i.e., the paper web 18 in the present example.

As shown to a greatly exaggerated extent in FIG. 3, the web 18 shrinks in the cross direction as it moves from the wet end of a papermaking process to the dry end. In this example, the width of the actuator control zone $S_1$ near the first actuator is much wider than the corresponding measurement zone of $S_1$ near the sensor frame 31. Furthermore, in practice, sheet shrinkage is not uniform from slice to slice and, instead, shrinkage is usually more pronounced for slices near the edge of a web than for slices near the middle of the web. Accordingly, a measure of the extent of the web cross-directional shrinkage of each control zone is defined as the ratio of the width at the dry end to the width at the wet end.

The present invention, as mentioned above, provides systems for automatically mapping and aligning control zones and measurement zones in sheetmaking systems by identifying the shrinkage of each control zones. A preliminary step in the process is to conduct bump tests by controllably displacing selected actuators. The objective in conducting the bump tests is to determine which measurement zone(s), or slice(s), correspond to which actuator control zone. Ultimately, data from the bump tests is used to construct shrink factor array that provide a set of coefficients for mapping, or transforming, measurement zones that are referenced to scanner frames to actuator zones referenced to profiling devices.

To conduct a bump test in the above-described system, at least one of the slice lip actuators is displaced from one operating point to another operating point while the resulting change in a sheet property is measured. In practice, it is preferred to bump several actuators simultaneously at scattered cross-direction locations but without simultaneously displacing adjacent actuators. To accomplish this, any two actuators that are simultaneously bumped should be at a sufficient distance from one another such that the response (induced change) of each displaced actuator is not significantly distorted by the coupling effect.

FIG. 4 shows the actual response magnitude versus set point of a slice lip actuator member from location $d_0$ to location $d_1$, $d_2$ and then back to $d_0$, as a function of time. To interpret this drawing, it should be understood that the actuator control signal is changed at times $t_0$, $t_2$ and $t_3$. The control signal that initiates the actuator bumps begin at time $t_0$. The set point path is the step function indicated by curve A in the drawing; however, the actual response path is more or less like the one indicated by curve B, with a time delay and a first order dynamic component.

After actuators are displaced (i.e., bumped) as described above, the change of cross-directional properties of a web can be measured and then assembled in a cross-directional profile. FIG. 5 shows one example of such a profile. The techniques for assembling such measurement profiles are quite well known, as are techniques for smoothing the profiles. The smoothing can be accomplished by noise filtering methods.

Various noise filtering techniques can be employed for smoothing measurement profiles. In one noise filtering process, for example, a curve which is representative of the displacement for one actuator is convolved onto an output signal from sensor 30. The convolution curve can be derived from, for instance, a model of the slice lip as shown in FIG. 6. As shown in that drawing, the slice lip is modeled as a flexible beam which is deformed by several actuators. The convolution curve can also simply be derived as a low pass filter according to any well known window, such as the Blackman window. The convolution curve, or window, must be symmetric to avoid phase-shift in the cross-direction.

The net result of such smoothing techniques is that, in the smoothed profiles, the peaks generally indicate the centers of measurement zones corresponding to the control zones with displaced actuators during the bump tests. The peak locations in the measurement profile could also be determined from a conventional analysis of the first and second derivatives of the measurement profiles.

As an example of the preceding discussion, FIG. 8A shows a profile which has been measured after a first bump test (the bold line) together with a profile which has been measured after a second bump test in the opposite direction (the lighter dashed line). FIG. 8B shows the center positions of the actuator zones selected for displacement. The positions are referenced to the profiling actuator devices. Corresponding to these positions, the peak positions of the profile in FIG. 8A will be taken as the centers of the corresponding measurement zone to specify, the mapping.

As mentioned above, shrinkage factors usually differ from slice to slice. Various techniques can be used for assigning shrinkage factors to control zones. FIG. 9A shows the case where, within each section of the web measured from the center of one bumped actuator zone (or measurement zone) to that of the next one, the shrinkage factors of all zones are assumed to be constant. FIG. 9B shows an approximation wherein the shrinkage factors are assumed to vary linearly within each section. Further, FIG. 9C shows an approximation wherein the measured shrinkage factors are approximated by continuous curve across the slices. For all types of approximations, it is preferred to that the total shrinkage of each section bounded by the two closest bumped zones remains the same.

As described above, the alignment data is acquired when the process is excited by an input profile that bumps the actuators sufficiently to slightly disturb the properties of the manufactured sheet product. In practice, the amplitude of the excitation can be adaptively adjusted for minimizing its effect upon the quality of the material being produced under the excitation. In practice, an excitation amplitude adapter adjusts the amplitude of the bump test actuator excitation profile so that the signal-to-noise ratio of the bump test response variations are sufficient to reveal the alignment properties relative to estimated noise. In practice, the root mean square (RMS) value of the response is calculated from the scanner-measured minislice profile variations prior to bump tests as compared to minislice profile variations after the bump tests.

The noise included in a bump test response can usually be estimated from the measured noise level before the bump test. In practice, the level of the excitation signal is selected based upon a preselected signal-to-noise ratio.

As mentioned above, the alignment data can be presented in the form of a shrink factor array. Each element of the array specifies the relative gain of width in the mapping the actuator zones to corresponding measurement zones. That is, the elements in a shrinkage factor array are ratio values that indicate the relative shrinkage of the slice versus the average overall shrinkage. For example, if a slice shrinks twice as much as the average slice, the coefficient in the shrink factor array for that slice would have the value 2. To determine an absolute value of the shrinkage for each slice in real time, the shrinkage factor array can be multiplied by the overall shrinkage of the sheet as determined by the measured sheet edges.

The above-described alignment system for mapping and aligning control zones and measurement zones in sheetmaking systems can be implemented by software operating in the profile analyzer 33. In practice, the software automatically acquires scanner-to-actuator alignment data (i.e., sheet position) and uses that data with the shrinkage array to construct a control profile, with each element of the control profile being the measurement at a measurement zone, for determining the control adjustments on the papermaking machine. In the preferred embodiment, the software includes the following component modules: an excitation generator, a bump test conductor, a test data analyzer, and an alignment data transformer. Also in practice, an excitation amplitude adapter is provided for adjusting the amplitude of the bump test actuator excitation profile as described above wherein, in conducting a bump test, a step function of predetermined amplitude is added to the setpoint of each of the selected cross-directional control actuators as the excitation input.

In practice, the actuator excitation profile is selected such that the variation across the web are rich in alignment data but do not include so much information that cross-coupling between the control zones and measurement zones distort the alignment information. The actuator excitation profile normally is designed so that the response minislice profile has a narrow frequency band spectrum. With a narrow frequency band spectrum, the useful alignment information is readily filtered from the noise by a bandpass (or lowpass) filter.

The bump test conductor includes a clock for scheduling events automatically at specified time periods. The fundamental time unit of the clock is usually selected as the time period between each two consecutive cross-directional scans. The scheduled events may include, for instance, starting providing the bump test actuator excitation profiles, collecting excitation response variation profiles, and starting a bump test data analysis sequence. In practice, the response variation profiles are accumulated and averaged for a specified number of scans beginning at a specified delay time after an actuator bump is initiated.

The test data analyzer typically comprises the cascade series of a profile smoother, a peak position locator, and a high resolution interpolator. The input to the analyzer is the response variation profile. The output of the analyzer provides an array containing the center position of each control zone corresponding to an actuator applied with a peak value of the actuator excitation profile.

The profile smoother preferably is a non-causal finite impulse response (FIR) bandpass filter which is applied to the response variation profile by convolution. In practice, the passband of the smoother includes the fundamental frequency of the response variation profile resulting from the bump test actuator excitation. Preferably, the smoother filter is selected such that its impulse response is symmetric, thereby avoiding spacial shifting in the cross direction. After smoothing, a cross-directional profile normally has one dominant peak within a neighborhood corresponding to each peak of the excitation profile, and the peaks are in the same order of distribution across the web. The corresponding positions found between the bumped actuators and the peaks of minislice measurements are used to construct the measurement mapping. That is, the positions of the peaks reveal the local alignment of control zones at different positions across the web.

The peak position locator operates to search for the minislices that support the dominant peak values of the response variation profile. In practice, maximum and minimum values are sought across the web through variation profiles as associated with excitation profiles. After being located, the minislice numbers corresponding to the located peak positions can be displayed in an array wherein each element corresponds to a given actuator.

Each element of the array obtained by the peak position locator expresses the center position of a measurement zone at the scanner corresponding to an actuator zone at the actuator device. The resolution of this expression is two minislices wide. In other words, the true center position of the measurement zone falls into a range in the center of the k'th minislice and the width of the range is twice the width of the minislice. In practice, more accurate position is determined by the peak position of a second order polynomial $Y(X)$. The polynomial $Y(X)$ is uniquely defined such that the curve $(X, Y(X))$ passes through the three points:

$(k-1, P_{k-1})(k, P_k)$ and $(k+1, P_{k+1})$ such that $Y(k+r) = P_{k+r}$, $r = -1, 0, 1$, where $P_k$ in the profile value at the minislice k.

As an alternative procedure, the location of the peak could be estimated by calculating the centroid of the area under each of the profiles.

The foregoing has described the principles, preferred embodiments, and modes of operation of the present invention. However, the invention should not be construed as limited to the particular embodiments discussed. Instead, the abovedescribed embodiments should be regarded as illustrative rather than restrictive, and it should be appreciated that variations may be made to those embodiments by workers who are skilled in the art without departing from the scope of the present invention as defined by the following claims.

What is claimed is:

1. A method for aligning control zones with measurement zones in a sheetmaking system having a plurality of actuators arranged in the cross-direction, comprising the steps of:

bumping at least one of the actuators;

measuring a profile of the sheet at a substantial distance from the bumped actuators by a scanner scanning the sheet;

determining the alignment information including the center location of the effect of each of the bumped actuators on the sheet by pattern matching between a cross-directional actuator excitation profile and its response profile measured by the scanner scanning the sheet; and providing the alignment information as a shrink factor array.

2. A method according to claim 1, wherein the bumping step includes adding a step input to the setpoint of each of the actuators as the excitation input.

3. A method according to claim 1 wherein, in the shrink factor array, each element of the array specifies relative shrinkage of a measurement zone that is to be mapped onto the corresponding actuator zone as a result of a bump test.

4. A method according to claim 1, wherein the coefficients in the shrinkage factor array are ratio values that indicate the relative shrinkage of the slice versus the average overall shrinkage.

5. A method according to claim 4, further comprising the step of removing noise from the measured profile.

6. A method according to claim 5, wherein the filtering step includes filtering the cross-direction profile with a symmetric (non-causal) finite impulse filter.

7. A method according to claim 1, wherein the determining step includes fitting a parabola curve to the measured profile.

8. A method according to claim 1, wherein the determining step includes adjusting the peak response positions.

9. A method according to claim 1 including the step of mapping control zones to aligned measurement zones.

10. A method of according to claim 9 wherein mapping includes interpolating the measured values.

11. A system for aligning control zones with measurement zones in a sheetmaking system having a plurality of actuators arranged in the cross-direction, the system comprising:

means for bumping at least one of the actuators;

means for measuring a profile of the sheet at a substantial distance from the bumped actuators;

means for determining the alignment information including the location of the effect of each of the bumped actuators on the sheet by pattern matching between the a cross-directional actuator excitation profile and its response profile measured by the scanner scanning the sheet; and means for providing the alignment information as a shrink factor array.

12. A system according to claim 11 wherein the means for providing the shrink factor array include means for specifying, as each element of the array relative shrinkage of a measurement zone that is to be mapped onto the corresponding actuator zone as a result of a bump test.

13. A system according to claim 11 wherein the bumping means includes means for providing a step function input to each of the actuators.

14. A system according to claim 11 wherein the actuators include at least one of slice lip actuators, steam boxes, calendar roll heating units, and water sprays, on paper making machines, and include die-bolts on plastic extruders.

15. A system according to claim 14 further comprising filter means for filtering noise from the measured profiles.

16. A system according to claim 15 wherein the noise filtering means includes a symmetric, non-causal finite impulse response filter.

* * * * *